United States Patent
Bowers et al.

(10) Patent No.: US 6,949,697 B2
(45) Date of Patent: Sep. 27, 2005

(54) SOYBEAN CULTIVAR S52-U3

(75) Inventors: Glenn R. Bowers, Jonesboro, AR (US); Karen M. Gallo, Jonesboro, AR (US); Howard L. Gabe, Uberlandia (BR)

(73) Assignee: Syngenta Participations AG, Basel (CH)

( * ) Notice: Subject to any disclaimer, the term of this patent is extended or adjusted under 35 U.S.C. 154(b) by 70 days.

(21) Appl. No.: 10/007,038

(22) Filed: Dec. 4, 2001

(65) Prior Publication Data

US 2003/0106087 A1 Jun. 5, 2003

(51) Int. Cl.$^7$ .............................. A01H 1/00; A01H 5/00; A01H 5/10; C12N 5/04
(52) U.S. Cl. ........................ 800/312; 800/260; 435/415
(58) Field of Search ................................. 800/312, 260, 800/300, 298, 302, 301, 266; 435/415, 430

(56) References Cited

U.S. PATENT DOCUMENTS 5,942,666 A * 8/1999 Rhodes ........................ 800/312
6,084,159 A * 7/2000 Luzzi ........................... 800/312

* cited by examiner

*Primary Examiner*—Anne Kubelik
(74) *Attorney, Agent, or Firm*—Bruce Vrana

(57) ABSTRACT

A novel soybean cultivar designated S52-U3 with high yield potential, tolerance to Roundup herbicide, early MG V maturity, and resistance to races 3, 9 and 14 of Soybean Cyst Nematode, further including the plants and seeds of the cultivar S52-U3, methods for producing a soybean plant by crossing the cultivar S52-U3 with itself or another soybean plant. The invention also relates to soybean cultivar S52-U3 further comprising one or more single gene traits, and to methods of producing a soybean having such traits by transformation or mutagenesis. The invention also includes using the soybean cultivar S52-U3 to produce other soybean cultivars or breeding lines.

11 Claims, No Drawings

SOYBEAN CULTIVAR S52-U3

FIELD OF THE INVENTION

The present invention is in the field of soybean breeding, specifically to a new and distinctive soybean cultivar, designated S52-U3.

BACKGROUND OF THE INVENTION

The present invention relates to a new and distinctive soybean cultivar, designated S52-U3. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. These important traits may include higher seed yield, resistance to diseases and insects, better stems and roots, tolerance to drought and heat, and better agronomic quality.

Soybeans [*Glycine max* (L.) Merr.] are recognized to be naturally self-pollinated plants, while capable of undergoing cross-pollination, rarely do so in nature. However, soybeans can be bred by both self-pollination and cross-pollination techniques. Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of a plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climate and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean cultivars, the crossing of these cultivars and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines as well as the phenotype of the hybrid influence to breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several F's. Selection of the best individuals may begin in the $F_2$ population; then, beginning in the $F_3$, the best individuals in the families are selected. Replicated testing of families can begin the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer, for special advertising and marketing, altered seed and commercial production practices, and new product utilization. The testing proceeding release of a new cultivar should take into consideration research and development costs as well as technical superiority of the final cultivar. For seed-propagated cultivars, it must be feasible to produce seed easily and economically.

Soybean, [*Glycine max* (L.) Merr.], is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

The present invention is a novel soybean cultivar designated S52-U3 with high yield potential, tolerance to Roundup herbicide, early MG V maturity, and resistance to races 3, 9 and 14 of Soybean Cyst Nematode. The invention relates to seeds of the cultivar S52-U3, plants of the cultivar S52-U3, and to methods for producing a soybean plant by crossing of the cultivar S52-U3 with itself or with another soybean genotype.

The invention is also directed to soybean cultivar S52-U3 further comprising one or more specific, single gene traits, for example transgenes, and which has essentially all of the morphological and physiological characteristics of cultivar S52-U3. The invention further relates to seeds of cultivar S52-U3 further comprising one or more specific, single gene traits. The invention also relates to plants of cultivar S52-U3 further comprising one or more specific, single gene traits. The invention includes methods for producing a soybean plant by crossing the soybean plant of cultivar S52-U3 further comprising one or more specific, single gene traits with itself or with another soybean genotype.

The invention is further directed to methods for producing a soybean plant by crossing a first parent soybean plant with a second parent soybean plant, wherein the first or second soybean plant is the soybean plant from the soybean line S52-U3. Further, both first and second parent soybean plants may be from the soybean cultivar S52-U3. Therefore, any methods using the soybean cultivar S52-U3 are part of this invention: selfing, backcrosses, hybrid breeding and crosses to populations. All plants produced using soybean cultivar S52-U3 as a parent are within the scope of the invention.

DEFINITIONS

In the description and tables that follow, a number of terms are used. In order to provide a clear and consistent understanding of the specification and claims, including the scope to be given such terms, the following definitions are provided:

Hypocotyl. A hypocotyl is the portion of an embryo or seedling between the cotyledons and the root. Therefore, it can be considered a transition zone between shoot and root.

Lodging Resistance. Lodging is rated on a scale of 1 to 9. Where one is completely upright and 9 is completely prostrate.

Maturity Date. Plants are considered mature when 95% of the pods have reached their mature color.

Phytophthora Root Rot Field Tolerance Score (PRR). PRR does not relate to race-specific vertical resistance, such as rps-1k or Rps6, but to horizontal, non-race specific resistance.

Plant Height. Plant height is taken from the top of soil to top of node of the plant and is measured in centimeters.

Pod. This refers to the fruit of a soybean plant. It consists of the hull or shell (pericarp) and the soybean seeds.

Pubescence. This refers to a covering of very fine hairs closely arranged on the leaves, stems and pods of the soybean plant.

Seed Yield (Bushels/Acre). The yield in bushels/acre is the actual yield of the grain at harvest.

DETAILED DESCRIPTION OF THE INVENTION

A soybean cultivar needs to be highly homogeneous, homozygous and reproducible to be useful as a commercial cultivar. There are many analytical methods available to determine the homozygotic and phenotypic stability of these cultivars.

The oldest and most traditional method of analysis is the observation of phenotypic traits. The data is usually collected in field experiments over the life of the soybean plants to be examined. Phenotypic characteristics most often observed are for traits associated with seed yield, lodging resistance, disease resistance, emergence, maturity, plant height, shattering, flower color, pubescence color, pod color and hilum color.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The cultivar of the invention has shown uniformity and stability for all traits, as described in the following cultivar description information. It has been self-pollinated a sufficient number of generations, with careful attention to uniformity of plant type to ensure homozygosity and phenotypic stability. The line has been increased with continued observation for uniformity. No variant traits have been observed or are expected in S52-U3. Soybean cultivar S52-U3, being substantially homozygous, can be reproduced by planting seeds of the line, growing the resulting soybean plants under self-pollinating or sib-pollinating conditions, and harvesting the resulting seed, using techniques familiar to the agricultural arts.

Publications useful as references in interpreting the data presented below include: Caldwell, B. E. ed. 1973. "Soybeans: Improvement, Production, and Uses" Amer. Soc. Agron. Monograph No. 16;Buttery, B. R., and R. I. Buzzell 1968. "Peroxidase Activity in Seed of Soybean Varieties" Crop Sci. 8: 722–725;Hymowitz, T. 1973. "Electrophoretic analysis of SBTI-A2 in the USDA Soybean Germplasm Collection" Crop Sci., 13: 420–421; Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

Soybean cultivar S52-U3 has the following morphological and other characteristics:

| | |
|---|---|
| Flower Color | White |
| Pubescence Color | Gray |
| Pod Color | Tan |
| Hilum Color | Buff |
| Seed Coat Color | Yellow |
| Leaf Shape | Ovate |
| Stem Termination | Determinate |
| Plant Type | Intermediate |
| Hypocotyl Color | Green |
| Maturity Group | V |
| Relative Maturity | 5.2 |
| Soybean Cyst Nematode | Resistant (R 3, 9, 14) |
| Southern Stem Canker | Moderate Resistance |
| Hypocotyl Length | Long |

The invention is further directed to methods for producing a soybean plant by crossing a first parent soybean plant with a second parent soybean plant, wherein the first or second soybean plant is the soybean plant from the soybean line S52-U3. Further, both first and second parent soybean plants may be from the soybean cultivar S52-U3. Therefore, any methods using the soybean cultivar S52-U3 are part of this invention: selfing, backcrosses, hybrid breeding and crosses to populations. All plants produced using soybean cultivar S52-U3 as a parent are within the scope of the invention.

The invention also encompasses plants of cultivar S52-U3 and parts thereof further comprising one or more specific, single gene transferred traits. Such traits are introgressed into cultivar S52-U3 from another soybean cultivar or are directly transformed into cultivar S52-U3. Preferably, one or more new traits are transferred to cultivar S52-U3, or, alternatively, one or more traits of cultivar S52-U3 are altered or substituted. The introgression of the trait(s) into cultivar S52-U3 is for example achieved by recurrent selection breeding, for example by backcrossing. The goal of a backcross protocol is to alter or substitute a single trait or characteristic in the original inbred. In one embodiment of the present invention, cultivar S52-U3 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes, i.e., will be like the recurrent parent for essentially all of the recurrent parent's physiological and morphological characteristics. (see, for example, Poehlman & Sleper (1995) Breeding Field Crops, 4th Ed., 172–175;Fehr (1987) Principles of Cultivar Development, Vol. 1: Theory and Technique, 360–376).

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity can be based on molecular markers used in the laboratory-based techniques described above.

The last backcross generation is then selfed to give pure breeding progeny for the gene(s) being transferred. The resulting plants have essentially all of the morphological and physiological characteristics of cultivar S52-U3, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

The cultivar of the invention can also be used for transformation where exogenous genes are introduced and expressed by the cultivar of the invention. Genetic variants created either through traditional breeding methods using cultivar S52-U3 or through transformation of cultivar S52-U3 by any of a number of protocols known to those of skill in the art are intended to be within the scope of this invention (see e.g. Trick et al. (1997) Recent advances in soybean transformation, in Plant Tissue Culture and Biotechnology, 3:9–26, incorporated herein by reference).

Production of a genetically modified plant tissue by transformation combines teachings of the present disclosure with a variety of techniques and expedients known in the art. In most instances alternate expedients exist for each stage of the overall process. The choice of expedients depends on the variables such as the plasmid vector system chosen for the cloning and introduction of the desired recombinant DNA molecule, as well as the particular structural gene, promoter elements and upstream elements used. Persons skilled in the art are able to select and use appropriate alternatives to achieve functionality. Culture conditions for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich et al., (Eds. pp. 89–119,CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Soybean & Soybean Improvement, 3rd Edition Sprague et al. (Eds. pp. 345–387) American Society of Agronomy Inc. et al. 1988.

Methods of introducing desired recombinant DNA molecule into plant tissue include the direct infection or co-cultivation of plant cells with *Agrobacterium tumefaciens*, Horsch et al., Science, 227:1229 (1985). Descriptions of Agrobacterium vector systems and methods for Agrobacterium-mediated gene transfer provided by Gruber, et al. supra. Other useful methods include but are not limited to expression vectors introduced into plant tissues using a direct gene transfer method such as microprojectile-mediated delivery, DNA injection, electroporation and the like. More preferably expression vectors are introduced into plant tissues using the biolistic microprojectile delivery or Agrobacterium-medicated transformation. Transformed plants obtained via protoplast transformation are also intended to be within the scope of this invention.

Many traits have been identified that are not regularly selected for in the development of a new cultivar but that can be improved e.g. by backcrossing techniques or by genetic transformation. Using materials and methods well known to those persons skilled in the art, traits that are capable of being transferred, to cultivar S52-U3 include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability, such as male sterility or male fertility, yield stability and yield enhancement. Other traits transferred to cultivar S52-U3 are for the production of commercially valuable enzymes or metabolites in plants of cultivar S52-U3.

Traits capable of being transferred to soybean cultivar S52-U3 are naturally occurring soybean traits or transgenic traits. Transgenes are directly introduced into cultivar S52-U3 using genetic engineering and transformation techniques well known in the art, some of which are described above, or are originally introduced into a donor, non-recurrent parent using genetic engineering and transformation techniques, which are then introgressed into cultivar S52-U3, for example by backcrossing. A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters preferably are used. The transgene may also comprise other regulatory elements such as for example translation enhancers or termination signals. In one embodiment of the present invention, the transgene nucleotide sequence in the cultivar S52-U3 includes a coding sequence that is transcribed and translated into a protein. In another embodiment of the invention, the nucleotide sequence encodes an antisense RNA or a sense RNA that is not translated or only partially translated.

Where more than one trait are introgressed into cultivar S52-U3, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover essentially all of the morphological and physiological characteristics of cultivar S52-U3 in addition to the multiple genes in the resulting soybean cultivar.

The genes responsible for a specific, single gene trait are generally inherited through the nucleus. Known exceptions are, e.g. the genes for male sterility, some of which are inherited cytoplasmically, but still act as single gene traits. In a preferred embodiment, a transgene to be introgressed into cultivar S52-U3 is integrated into the nuclear genome of the donor, non-recurrent parent or the transgene is directly transformed into the nuclear genome of cultivar S52-U3. In another preferred embodiment, a transgene to be introgressed into cultivar S52-U3 is integrated into the plastid genome of the donor, non-recurrent parent or the transgene is directly transformed into the plastid genome of cultivar S52-U3. In a preferred embodiment, a plastid transgene comprises one gene transcribed from a single promoter or two or more genes transcribed from a single promoter.

A non-exclusive list of traits or nucleotide sequences capable of being transferred into cultivar S52-U3, using material and methods well known to those persons skilled in the art are as follows: genetic factor(s) responsible for resistance to brown stem rot (U.S. Pat. No. 5,689,035) or resistance to cyst nematodes (U.S. Pat. No. 5,491,081); a transgene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137-41;a herbicide tolerance transgene whose expression renders plants of cultivar S52-U3 tolerant to the herbicide, for example, expression of an altered acetohydroxyacid synthase (AHAS) enzyme confers upon plants tolerance to various imidazolinone or sulfonamide herbicides (U.S. Pat. No. 4,761,373). Other such traits include, for example, a non-transgenic trait conferring to cultivar S52-U3 tolerance to imidazolinones or sulfonylurea herbicides; a transgene encoding a mutant acetolactate synthase (ALS) that render the plants resistant to inhibition by sulfonylurea herbicides (U.S. Pat. No. 5,013,659); a gene encoding a mutant glutamine synthetase (GS) resistant to inhibition by herbicides that are known to inhibit GS, e.g. phosphinothricin and methionine sulfoximine (U.S. Pat. No. 4,975,374); and a *Streptomyces bar* gene encoding a phosphinothricin acetyl transferase resulting in tolerance to the herbicide phosphinothricin or glufosinate (U.S. Pat. No. 5,489,520). Other traits capable of being transferred to the cultivar S52-U3 of the invention include toleration to inhibition by cyclohexanedione and aryloxyphenoxypropanoic acid herbicides (U.S. Pat. No. 5,162,602), which is conferred by an altered acetyl coenzyme A carboxylase(ACCase); transgenic glyphosate tolerant plants, which tolerance is conferred by an altered 5-enolpyruvyl-3-phosphoshikimate (EPSP) synthase gene; tolerance to a protoporphyrinogen oxidase inhibitor, which is achieved by expression of a tolerant protoporphyrinogen oxidase enzyme in plants (U.S. Pat. No. 5,767,373). In yet another embodiment of the present invention, a transgene introgressed into cultivar S52-U3 comprises a gene conferring tolerance to a herbicide and at least another nucleotide sequence for another trait, such as for example, insect resistance or tolerance to another herbicide.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which do not have the desired herbicide tolerance characteristic, and only those plants which have the herbicide tolerance gene are used in the subsequent backcross. This process is then repeated for the additional backcross generations.

This invention is also directed to methods for producing a soybean plant by crossing a first parent soybean plant with a second parent soybean plant, wherein the first or second soybean plant is the soybean plant from the line S52-U3. Further, both first and second parent soybean plants may be from the cultivar S52-U3. Therefore, any methods using the cultivar S52-U3 are part of this invention: selfing, backcrosses, hybrid breeding, and crosses to populations. Any plants produced using cultivar S52-U3 or cultivar S52-U3 further comprising one or more specific, single gene traits as a parent are within the scope of this invention. For example, the soybean cultivar S52-U3 or cultivar S52-U3 further comprising one or more specific, single gene traits are used in crosses with other, different, soybean plants to produce first generation (F1) soybean hybrid seeds and plants with superior characteristics. For example, a method to produce a hybrid soybean seed comprises the steps of planting, preferably in pollinating proximity, seeds of soybean cultivar S52-U3 or seeds of soybean cultivar S52-U3 further comprising one or more specific, single gene traits and another soybean cultivar, cultivating the soybean plants resulting from said seeds until said plants bear flowers, emasculating the plants of either one or the other soybean cultivar, inducing cross pollination to occur between said soybean cultivars and harvesting seeds produced on said emasculated plants of the cultivar line.

As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like. Thus, another aspect of this invention is to provide for cells that upon growth and differentiation produce the cultivar S52-U3.

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet. (1991) 82:633–635;Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103–113 (1992); Dhir, S. et al., "Regeneration of Fertile Plants from Protoplasts of Soybean (*Glycine max* L. Merr.): Genotypic Differences in Culture Response," Plant Cell Reports (1992) 11:285–289;Pandey, P. et al., "Plant Regeneration from Leaf and Hypocotyl Explants of *Glycine wightii* (W. and A.) VERDC. var longicauda," Japan J. Breed. 42:1–5 (1992); and Shetty, K., et al., "Stimulation of In Vitro Shoot Organogenesis in *Glycine max* (Merrill.) by Allantoin and Amides," Plant Science 81:(1992) 245–251;as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells which upon growth and differentiation produce soybean plants having all or essentially all the physiological and morphological characteristics of cultivar S52-U3. The disclosures, publications, and patents which are disclosed herein are all hereby incorporated herein in their entirety by reference.

INDUSTRIAL APPLICABILITY

The seed of soybean cultivar S52-U3 further comprising one or more specific, single gene traits, the plant produced from the seed, the hybrid soybean plant produced from the crossing of the cultivar with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990. Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein. For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A seed of soybean cultivar designated S52-U3, representative seed of said soybean cultivar having been deposited under ATCC Accession No: PTA-5164.

2. A soybean plant, or a part thereof, produced by growing the seed of claim 1.

3. Pollen of the plant of claim 2.

4. An ovule of the plant of claim 2.

TABLE

Comparison Between S52-U3 and Syngenta 3474, Syngenta S51-T1, Syngenta S53-Q7 and Pioneer 9511

| Cultivar/Trait | Yield | Maturity | Lodging | Height | PRR | IC | SDS | R3 | R14 |
|---|---|---|---|---|---|---|---|---|---|
| S52-U3 | 42.7 | 10–6 | 3.6 | 88 | 3.5 | 4.3 | 4.0 | R | R |
| Syngenta 3474 | 44.0 | 9–26 | 4.5 | 105 | 3.3 | 7.3 | 2.1 | S | S |
| Syngenta S51-T1 | 37.7 | 10–5 | 4.2 | 128 | 3.8 | 5.3 | 4.4 | MR | S |
| Syngenta S53-Q7 | 38.6 | 10–7 | 2.5 | 90 | 4.5 | 2.5 | 3.5 | R | MR |
| Pioneer 9511 | 42.0 | 10–3 | 2.8 | 113 | 4.2 | 3.8 | 5.0 | | |
| Grand Mean | 41.0 | | 3.5 | 105 | 3.9 | 4.6 | 3.8 | | |
| No. of Tests | 37 | 17 | 20 | 23 | 2 | 2 | 3 | | |
| LSD (0.05) | 2.7 | 2 | 0.7 | 7 | 2.9 | 3.1 | 2.6 | | |

Yield, bushels per acre;
Maturity, date, 95% mature pod color;
Lodging, 1 = upright, 9 = prostrate;
Height, cm., ground level to plant top;
PRR, 1 = highly tolerant, 9 = highly intolerant;
IC, 1 = highly resistant, 9 = highly susceptible;
Sudden Death Syndrome (SDS), 1 = no foliar symptoms, 9 = severe symptoms;
S = susceptible;
R = resistant;
MR = moderately resistant

DEPOSIT INFORMATION

Applicant has made a deposit of at least 2500 seeds of the cultivar of the present invention with the American Type Culture Collection (ATCC), Manassas, Va., 20110-2209 U.S.A., ATCC Accession Number No: PTA-5164. During pendency of this application, access to the invention will be afforded to the Commissioner by request; all restrictions upon availability to the public will be irrevocably revoked upon granting of the patent; the deposit of cultivar S52-U3 will be maintained in the ATCC depository, which is a public depository, for a period of 30 years, or 5 years after the most recent request, or for the effective life of the patent, whichever is longer, and will be replaced if it becomes nonviable during that period. Applicant has tested the viability of the deposit at the time of deposit. Applicant has satisfied all the requirements of 37 C.F.R. §§1.801–1.809. Applicant 5. A soybean plant, or a part thereof, having all the physiological and morphological characteristics of the plant according to claim 2.

6. A seed produced by self-pollinating and growing the plant according to claim 2 or 5.

7. A tissue culture of regenerable cells of the soybean plant according to claim 2 or 5.

8. The tissue culture according to claim 7, wherein the cells of said tissue culture are from a plant part selected from the group consisting of a leaf, a pollen, an embryo, a root, a flower, a pod, and a stem.

9. A method for producing a soybean seed, wherein the method comprises crossing a first parent soybean plant with a second parent soybean plant and harvesting the resultant soybean seed, wherein said first or second parent soybean plant is the soybean plant according to claim 2 or 5.

10. The method for producing a soybean seed according to claim 9, further comprising the step of growing said seed to produce a progeny soybean plant.

11. A method for producing a S52-U3-derived soybean plant, wherein the method comprises:

a) crossing inbred soybean line S52-U3, representative seed of which have been deposited under ATCC Accession No: PTA-5164, with a second soybean plant to yield progeny soybean seed; and b) growing said progeny soybean seed to yield said S52-U3-derived soybean plant.

* * * * *